US011136561B2

(12) United States Patent
Torres Acosta et al.

(10) Patent No.: US 11,136,561 B2
(45) Date of Patent: Oct. 5, 2021

(54) POLYPEPTIDE FOR THE ENZYMATIC DETOXIFICATION OF ZEARALENONE, ISOLATED POLYNUCLEOTIDE, AND ASSOCIATED ADDITIVE, USE AND METHOD

(71) Applicant: Erber Aktiengesellschaft, Traismauer (AT)

(72) Inventors: Juan Antonio Torres Acosta, Vienna (AT); Gerhard Adam, Vienna (AT); Elisavet Kunz-Vekiru, Vienna (AT); Wulf-Dieter Moll, Stockerau (AT); Rudolf Mitterbauer, Scheffau am Wilden Kaiser (AT); Clemens Schmeitzl, Vienna (AT)

(73) Assignee: ERBER AKTIENGESELLSCHAFT, Traismauer (AT)

( * ) Notice: Subject to any disclaimer, the term of this patent is extended or adjusted under 35 U.S.C. 154(b) by 0 days.

(21) Appl. No.: 16/829,204

(22) Filed: Mar. 25, 2020

(65) Prior Publication Data
US 2020/0332269 A1 Oct. 22, 2020

Related U.S. Application Data

(62) Division of application No. 15/524,643, filed as application No. PCT/AT2015/000138 on Nov. 4, 2015, now abandoned.

(30) Foreign Application Priority Data

Nov. 7, 2014 (AT) .................................. A 816/214
Aug. 17, 2015 (AT) ................................. A 538/2015

(51) Int. Cl.
C12P 17/08 (2006.01)
C12N 9/02 (2006.01)
C12N 1/19 (2006.01)
C12N 15/53 (2006.01)
C12N 15/82 (2006.01)
C12N 15/81 (2006.01)

(52) U.S. Cl.
CPC ........... *C12N 9/0073* (2013.01); *C12N 15/81* (2013.01); *C12N 15/82* (2013.01); *C12N 15/8242* (2013.01); *C12P 17/08* (2013.01); *C12Y 114/13022* (2013.01)

(58) Field of Classification Search
None
See application file for complete search history.

(56) References Cited

U.S. PATENT DOCUMENTS

2010/0192985 A1* 8/2010 Aehle ................ C11D 3/38645
134/26
2018/0298352 A1* 10/2018 Torres Acosta ......... C12P 17/08

FOREIGN PATENT DOCUMENTS

WO 01/42436 A2 6/2001
WO 03/053161 A1 7/2003

OTHER PUBLICATIONS

Torres Acosta et al., "Proceedings of the 2014 National Fusarium Head Blight Forum", p. 47, Dec. 2014 (Year: 2014).*
International Search Report, dated Jun. 9, 2016.
Molnar et al., "*Trichosporon mycotoxinivorans* sp. nov., A New Yeast Species Useful in Biological Detoxification of Various Mycotoxins", Systematic and Applied Microbiology, vol. 27, Dec. 15, 2004, pp. 661-671, cited in the ISR.
G. Schatzmayr et al., "Detoxification of mycotoxins by biotransformation", The mycotoxin factbook, Jan. 1, 2006, pp. 363-375, cited in the ISR.
Vekiru et al., "Cleavage of Zearalenone by *Trichosporon mycotoxinivorans* to a Novel Nonestrogenic Metabolite", Applied and Environmental Microbiology, vol. 76, No. 7, Apr. 1, 2010, pp. 2353-2359, cited in the ISR.
Takahashi-Ando et al., "A novel lactonohydrolase responsible for the detoxification of zearalenone: enzyme purification and gene cloning", Biochemical Journal, vol. 365, Jul. 1, 2002, pp. 1-6, cited in the ISR.
Zinedine et al., "Review on the toxicity, occurrence, metabolism, detoxification, regulations and intake of zearalenone: An oestrogenic mycotoxin", Food and Chemical Toxicology, vol. 45, Nov. 25, 2006, pp. 1-18, cited in the ISR.
Pazmino et al., "Self-Sufficient Baeyer-Villiger Monooxygenases: Effective Coenzyme Regeneration for Biooxygenation by Fusion Engineering", Angewandte Chemie International Edition, vol. 47, No. 12, Mar. 7, 2008, pp. 2275-2278, cited in the ISR.

* cited by examiner

*Primary Examiner* — David Steadman
(74) *Attorney, Agent, or Firm* — Jacobson Holman PLLC (57) ABSTRACT

The invention relates to a polypeptide for the enzymatic detoxification of zearalenone, said polypeptide being a monooxygenase which converts the keto group in position 7 of zearalenone into an ester group, the monooxygenase in particular being an amino acid sequence selected from the group comprising sequence ID No. 1, 2 and 3 or a functional variant thereof. The functional variant and at least one of the amino acid sequences has a sequence identity of at least 60%, preferably at least 70%, more preferably at least 80% and most preferably 90%.

2 Claims, 2 Drawing Sheets

Specification includes a Sequence Listing.

POLYPEPTIDE FOR THE ENZYMATIC DETOXIFICATION OF ZEARALENONE, ISOLATED POLYNUCLEOTIDE, AND ASSOCIATED ADDITIVE, USE AND METHOD

This is a divisional application of application Ser. No. 15/524,643, filed May 5, 2017, which in turn is a U.S. national stage application of PCT/AT2015/000138, filed Nov. 4, 2015 and published in German, claiming the priority benefit of Austrian No. A 816/2014, filed Nov. 7, 2014 and Austrian Patent Application No. 2006-21315, filed Aug. 17, 2015, all of which are hereby incorporated by reference.

BACKGROUND OF THE INVENTION

The present invention relates to a polypeptide for the enzymatic detoxification of zearalenone, a transgenic host cell for the preparation of a zearalenone-detoxifying monooxygenase, an additive for the enzymatic detoxification of zearalenone, and the use of an isolated polynucleotide, and a method for preparing a zearalenone-detoxifying monooxygenase.

Mycotoxins are secondary metabolites produced by filamentous fungi. An important representative of the same is the widespread zearalenone (ZEN), formerly known as F-2 toxin, which is produced by a plurality of *Fusarium* fungi. These fungi inter alia infest cultivated plants such as various cereal crops, fungal infestation usually occurring prior to the harvest, wherein the growth of the fungi, or production of mycotoxins my also occur prior to the harvest or, with improper storage, even after the harvest. FAO estimates that, on a global scale, 25% of the agrarian products are contaminated with mycotoxins, which results in considerable economic losses. In a study recently performed worldwide, a total of 23,781 samples were analyzed from January 2009 to 2011, 81% having been tested positive for at least one mycotoxin and 45% having been tested positive for ZEN. ZEN was found at a frequency of up to 100% in all regions of the world and in all tested cereal and feed classes such as maize, soy meal, wheat, wheat bran, DDGS (distillers dried grains with solubles) as well as in finished animal feed mixtures.

ZEN is a non-steroidal, estrogenic, macrocyclic lactone synthesized via the polyketide metabolic pathway and having the structural formula:

and the IUPAC nomenclature naming (2E,11D)-15,17-dihydroxy-11-methyl-12-oxabicyco[12.4.0]octadeca-1(18),2,14,16-tetraene-7,13-dione. There are different nomenclatures for ZEN and ZEN metabolites, the nomenclature of Metzler (2011, Mycotox. Res., 27:1-3) having been adopted in this document as far as possible. Besides ZEN, a plurality of ZEN derivatives formed by enzymatic or chemical modifications of ZEN also occur in nature. Furthermore, ZEN metabolites are inter alia formed in the human or animal organism.

ZEN as well as ZEN derivatives such as α-ZEL or β-ZEL are also detectable in processed food or feed products, such as bread, beer or DDGS, due to their high chemical and physical stability.

Although ZEN comprises a relatively low acute toxicity and an oral LD50 value of up to 20,000 mg/kg body weight, subacute and/or subchronic toxic effects such as teratogenic, carcinogenic, immunosuppressive and estrogenic effects may occur in animals or humans after extended intake. ZEN binds to the estrogen receptor and may cause hormonal disorders, and hence a reduction of the formed metabolites as compared to ZEN is usually understood by detoxification of zearalenone.

The intake of feeds contaminated with ZEN results in development disorders in mammals, pigs and, in particular, young animals, being extremely sensitive to ZEN. ZEN concentrations above 0.5 ppm in feeds will lead to development disorders, wherein, for instance, concentrations above 1.5 ppm may lead to hyper-estrogenicity in pigs, and concentrations of 12 ppm have been made responsible for bovine miscarriages. Since zearalenone is rapidly absorbed via mucous membranes, in particular via the mucous membranes of the stomach, yet also of the mouth, an immediate and, above all, quantitative detoxification is necessary. Already 30 minutes after the oral administration of ZEN, the latter is detectable in blood. In order to achieve as complete a detoxification as possible, the use of isolated enzymes was found to be advantageous over microorganisms, the former exhibiting a higher specific activity or more rapid action. Due to the harmful effect of ZEN, the European Union established binding upper limits of ZEN in foods and gave recommendations for ZEN upper limits in feeds (EC NO: 1881/2006).

The primary strategy for reducing ZEN contamination in foods or feeds is to restrict the growth of fungi, for instance by observing "good agricultural practices". These includes seeds free of pests and fungal infestation, or the removal of agricultural waste products from fields in due time. Furthermore, the growth of fungi in the fields can be reduced by the use of fungicides. After the harvest, the crop should be stored at a residual moisture of below 15% and a low temperature in order to prevent the growth of fungi. Similarly, items contaminated by fungal infestation should be removed prior to further processing. Despite this list of measures, I. Rodriges and K. Naehrer reported (2012) that even in regions with the highest agricultural standards, such as the USA and Central Europe, 29% and 39%, respectively, of the tested maize samples were contaminated with ZEN from 2009 to 2011.

Other options for removing ZEN from feeds or foods comprise the adsorption or the transformation of the mycotoxin. To this end, it is necessary that the binding of the mycotoxin to the adsorbent is strong and specific over a wide pH range and remains stable in the entire gastrointestinal area throughout the digestive process. Although some non-biological adsorbents such as activated carbon, silicates or synthetic polymers like cholestryamine can be efficiently used for aflatoxins, their use for other mycotoxins is limited. The essential disadvantage of adsorbents is the non-specific binding of other molecules partially essential for nutrition. Biological adsorbents such as yeast or yeast extracts are also described in the literature, yet are similarly limited as non-biological adsorbents.

The detoxification of ZEN by physical and chemical treatments is also limited. ZEN cannot be effectively deactivated by thermal treatment, yet the ZEN content can be reduced by 83.9% by extrusion and treatment with oxidants, e.g. for 16 hours at 80° C. with a 10% hydrogen peroxide solution. The use of extrusion methods and oxidants like ozone or hydrogen peroxide in the production of feeds and foods is limited due to the high costs, loss of quality, sometimes low efficiency and low specificity involved.

DESCRIPTION OF RELATED ART

From EP 0 938 575 B1, ZEN-degrading properties of bacteria of the genus Rhodococcus and Nocardia, in particular R. globerulus, R. erythropolis and N. globerula, are known.

Vekiru et al. (Appl. and Environ. Microb., 2010, 76, 7, 2353-2359) describes the biotransformation of ZEN to the less estrogenic metabolite ZOM-1 by the microorganisms Trichosporon mycotoxinivorans.

The terms used below are taken from the technical terminology and, unless otherwise stated, are each used in their conventional meanings. Thus, the term "polynucleotide" refers to any kind of genetic material of any length and sequence, such as single-stranded and double-stranded DNA and RNA molecules, including regulatory elements, structural elements, groups of genes, plasmids, entire genomes and fractions thereof. The term "polypeptide" comprises proteins such as enzymes, antibodies and polypeptides with up to 500 amino acids, such as peptide inhibitors, domains of proteins, yet even short polypeptides with small sequence lengths, e.g. less than 10 amino acids, such as receptors, ligands, peptide hormones, tags and the like. The term "position" in a polynucleotide or polypeptide refers to a single, specific base or amino acid in the sequence of said polynucleotide or polypeptide, respectively.

BRIEF SUMMARY OF THE INVENTION

The present invention aims to provide a polypeptide that enables the rapid and reliable conversion of zearalenone to a zearalenone derivative whose toxicity and estrogenic effect are reduced to such an extent as to be able to remain in feeds or food products while being harmless to the respective end users.

To solve this object, the present invention is essentially characterized in that the polypeptide is a monooxygenase converting the keto group in position 7 of zearalenone into an ester group, and that the polypeptide comprises an amino acid sequence selected from the group consisting of SEQ ID Nos. 1, 2 and 3 or a functional variant thereof, the functional variant and at least one of the amino acid sequences having a sequence identity of at least 60%, preferably at least 70%, more preferably at least 80%, and most preferably at least 90%. Monooxygenases are enzymes belonging to group I of the EC classification, which catalyze the incorporation of an oxygen atom from $O_2$ into the respective substrate, i.e. zearalenone in the present case. More particularly, in the case of zearalenone, an oxygen atom is incorporated in position 7 of the ring structure of zearalenone, thus obtaining a less strongly toxic zearalenone derivative (iZOM). Surprisingly, it has been found that such detoxification occurs in just a single enzymatic reaction step, and that the reaction product iZOM has a toxicity that is lower by a factor of about 100, and virtually no longer exhibits an estrogenic effect, despite the closed ring structure still present and the carbon oxygen double bond in position 7.

A particularly complete conversion of zearalenone into the less toxic derivative iZOM will be possible if the polypeptide is an amino acid sequence selected from the group consisting of SEQ ID1, 2 and 3 or a functional variant thereof, the functional variant and at least one of the amino acid sequences having a sequence identity of at least 60%, preferably at least 70%, more preferably at least 80%, and most preferably at least 90%. Due to the presence of at least one such conserved amino acid sequence, such as the sequences of ID Nos. 1, 2 and 3, or a functional variant thereof, it is possible to provide a polypeptide which, in addition to the rapid and complete conversion of ZEN, also comprises a particularly high activity value as compared to hitherto known ZEN-transforming polypeptides.

It has so far been assumed that a cleavage of the lactone ring system is required for an efficient detoxification of ZEN. It has, however, been surprisingly found that an effective detoxification will also be achieved by the conversion of the keto group in position 7 of zearalenone to an ester group, during which rearrangement no cleavage of the ring system takes place.

According to a further development of the invention, the monooxygenase is selected such that it is a Baeyer-Villiger monooxygenase. The use of a Baeyer-Villiger monooxygenase ensures that the reaction will exclusively occur at the desired position 7, since this is the only site accessible for a so-called Baeyer-Villiger oxidation, i.e. the conversion of a ketone to an ester by incorporating an oxygen atom.

According to a further development of the invention, the polypeptide is selected such that the polypeptide, in particular the monooxygenase, converts zearalenone to iZOM in a one-step enzymatic oxidation reaction so as to detoxify at least 70% of the zearalenone within 24 hours at 30° C. by converting the keto group in position 7 of the zearalenone into an ester group, said polypeptide being formed by a transformed yeast strain YZGA515, which is transformed with a pCS57 vector additionally containing a polynucleotide for expressing the polypeptide, and the transformed yeast strain is used at a cell density OD600 of 4, and zearalenone is used as a substrate at a concentration of 2 mg/l, and SC-LEU medium is used as a reaction medium. This is, in particular, feasible because the reaction product iZOM surprisingly has a toxicity reduced by a factor of about 100.

Due to the specific structure of the zearalenone molecule and, in particular, due to the keto group present in position 7 of the zearalenone molecule, the selective incorporation of the desired oxygen atom in position 7 of the zearalenone by a subgroup consisting of the Baeyer-Villiger monooxygenase, namely cyclohexanone monooxygenase, has become possible, as in correspondence with a further development of the invention. The ester group formed by such incorporation in a surprising manner causes the formed cyclic metabolite (iZOM) to have a significantly reduced toxicity as compared to zearalenone.

ZEN

-continued

[Chemical structure: iZOM]

By the term "sequence identity", a percental identity is understood. For amino acid sequences and nucleotide sequences, the relative sequence identity can be determined visually, yet preferably calculated by a computer program. The amino acid sequences of SEQ ID Nos. 1, 2 and 3, and the nucleotide sequences of SEQ ID Nos. 3, 4 and 5 are defined as reference sequences. A sequence comparison is also performed within sequence sections, a section meaning a continuous sequence of the reference sequence. Normally, the length of the sequence sections for nucleotide sequences is 18 to 600, preferably 45 to 200, more preferably 100 to 150, nucleotides. Normally, the length of the sequence sections for peptide sequences is 3 to 200, more preferably 15 to 65, most preferably 30 to 50, amino acids. There is a plurality of purchasable or costlessly available bioinformatic programs that can be used for the determination of homology and are constantly updated. Examples include GCG Wisconsin Bestfit package (Devereux et al. 1984), BLAST (Altschul et al. 1990) or BLAST 2 (Tatusova und Madden 1999). Due to different adjustment options of these algorithms, it may happen that different results are output at identical input sequences, which is why such algorithms and the associated adjustments have to be defined. In the present case, the sequence identity was performed using the programs NCBI BLAST (Basic Local Alignment Search Tool), in particular BLASTP for polypeptides and BLASTN for polynucleotides, in the versions of Oct. 20, 2014, which are available on the website of the National Center for Biotechnology Information (NCBI; www.ncbi.nlm.nih.gov). It is thereby possible to compare two or several sequences with one another according to the algorithm of Altschul et al., 1997 (Nucleic Acids Res., 25: 3389-3402). In this case, the programs versions of May 15, 2013, were used. As program adjustments, the base adjustments were applied, yet, in particular, for the amino acid comparison: "max target sequence"=100; "expected threshold"=10; "word size"=3; "matrix"=BLOSOM62; "gap costs"="Existence: 11; Extension: 1"; "computational adjustment"="Conditional compositional score matrix adjustment"; and for the nucleotide sequence comparison: Word Size: 11; Expect value: 10; Gap costs: Existence=5, Extension=2; Filter=low complexity activated; Match/Mismatch Scores: 2, -3; Filter String: L; m.

The terms "functional polypeptide variant" or "functional variant", on the one hand, refer to "allelic variants" of the polypeptide and to "functional fragments" of the polypeptide and, on the other hand, refer to a "modified polypeptide", wherein the enzymatic function is substantially unchanged as compared to the polypeptide of SEQ ID No.1. The term "allelic variant" refers to a polypeptide that was formed by nucleotide sequence mutation(s) accidentally occurring in nature and causes a change in the amino acid sequence, wherein the enzymatic function is unaffected thereby. The term "functional fragment" relates to a part or partial sequence of a polypeptide, or a part or partial sequence of a functional variant thereof, wherein the enzymatic function is substantially maintained. "Modified polypeptides" may comprise C- or N-terminal fusion proteins or selectively mutated polypeptides, mutations being obtainable by the substitution, insertion or deletion of at least one amino acid and, in particular, by site-specific mutagenesis or accidental mutagenesis, recombination and/or any other protein-engineering method, wherein the enzymatic function is substantially maintained. The terms substitution, insertion and deletion are used in the meanings common in genetic engineering and familiar to the skilled artisan. An enzymatic function is substantially maintained if the enzymatic reaction mechanism remains unchanged, i.e. the keto group in position 7 of the mycotoxin ZEN is converted to a corresponding ester group as shown in the above-mentioned reaction mechanism, and the specific residual activity is at least 5%, preferably at least 10%, in particular at least 50%, based on the original polypeptide.

Polypeptides having amino acid sequences SEQ ID Nos. 1 and 3 are functional allelic variants, with the sequences each derived from different microorganisms. This is clearly apparent from the close relative relationship, measured by the percentual sequence identity, and from the fact that the polypeptides act on ZEN by the same mechanism. The polypeptide of SEQ ID No. 1 is completely contained in the sequence SEQ ID No. 2, yet the polypeptide of SEQ ID No. 2 comprises an N-terminus extended by 28 amino acids.

By the terms "detoxification" or "detoxify", a reduction of the estrogenic activity of ZEN is understood. The measurement of the estrogenic activity is preferably performed according to the method described in the exemplary embodiments. Other methods may, however, also be applied, the decisive factor always being a reduction of the estrogenic activity of ZEN by its enzymatic conversion to iZOM. Measured by the estrogenicity assay described in the exemplary embodiments, iZOM has an estrogenic activity lower than that of ZEN by a factor of about 100.

Moreover, an isolated polynucleotide can be provided, by which it is possible to prepare a polypeptide for the rapid and reliable detoxification of ZEN. To this end, the isolated polynucleotide has a nucleotide sequence encoding a polypeptide that is a monooxygenase converting the keto group in position 7 of zearalenone into an ester group, and/or has a degree of sequence identity of at least 60% with at least one nucleotide sequence selected from the group consisting of SEQ ID Nos. 4, 5 and 6. In this case, the nucleotide sequence is able to hybridize, under medium stringency conditions, with at least one nucleotide sequence selected from the group consisting of SEQ ID Nos. 4 to 6 and/or a partial sequence thereof of at least 200 nucleotides, in particular at least 100 nucleotides, and/or a complementary strand of the nucleotide sequence or partial sequence thereof. The expression of such a polynucleotide ensures that the resulting polypeptide transforms ZEN into iZOM.

Nucleotide sequences to be expressed, in particular their triplets (codons), are usually changed as a function of their host cell such that the codon bias is optimized as a function of the host cell. This results in that even polynucleotides having a degree of sequence identity of far below 80%, yet even below 70% or below 60%, will be able to encode one and the same polypeptide. A sequence comparison for determining the degree of sequence identity must also be performed within sequence sections, a section meaning a continuous sequence of the reference sequence. Normally, the length of sequence sections for nucleotide sequences is 15 to 600.

By the aid of the present isolated nucleotide sequences or sequence sections, it has become possible to generate nucleic acid probes having lengths of usually at least 15, 30 or 40 nucleotides. Such nucleotide sequences, which are referred to as probes and in most cases are additionally labeled, e.g. with $^3$H, $^{32}$P, $^{35}$S, biotin or avidin, can be identified by applying standard method nucleotide sequences encoding polypeptides with ZEN-degrading activity. DNA, RNA or cDNA of individual microorganisms, genomic DNA libraries or cDNA libraries can, for instance, be used as starting materials for the identification of such sequences.

For nucleotide sequences having lengths of at least 100 nucleotides, medium stringency conditions are defined as prehybridization or hybridization at 42° C. in a five-fold NaCl-containing Na-EDTA buffer (SSPE, 0.9 M NaCl, 60 mM NaH$_2$PO$_4$, 6 mM EDTA) containing 0.3% sodium dodecyl sulfate (SDS), 200 μg/ml sheared and denaturated salmon sperm DNA and 35% formamide, followed by standard Southern Blot conditions, wherein the carrier material is finally washed three times with double sodium chloride citrate buffer (SSC, 300 mM NaCl and 30 mM trisodium citrate, 0.2% SDS) at 55° C. for 15 minutes.

For nucleotide sequences having lengths of 15 to 100 nucleotides, medium stringency conditions are defined as prehybridization or hybridization in a buffer comprising 0.9 M NaCl, 0.09 M Tris-HCl pH=7.6, 6 mM EDTA, 0.5% NP-40, single Denhardt's solution, 1 mM sodium pyrophosphate, 1 mM sodium dihydrogen phosphate, 0.1 mM ATP and 0.2 mg/ml yeast RNA, wherein said prehybridization and hybridization are effected at temperatures of 5° C. to 10° C. below the calculated melting temperatures (Tm), Tm being determined by calculation according to Bolton and McCarthy (1962, Proceedings of the National Academy of Sciences USA 48:1390). After this, the test is continued under standard Southern Blot conditions (J. Sambrook, E. F. Fritsch and T. Maniatis, 1989, Molecular Cloning, A Laboratory Manual, 2nd edition, Cold Spring Harbor, New York). The carrier material is finally washed once with a six-fold sodium chloride citrate buffer containing 0.1% SDS for 15 minutes and twice with a six-fold SSC buffer, each for 15 minutes at 5° C. to 10° C. below the calculated Tm.

Another object of the invention is to provide a transgenic host cell for preparing a zearalenone-detoxifying monoxygenase.

To solve this object, the invention is essentially characterized in that the host cell expresses a polynucleotide, that the polynucleotide comprises a nucleotide sequence encoding at least one polypeptide according to the claims and having a degree of sequence identity of at least 60% with at least one nucleotide sequence selected from the group consisting of SEQ ID Nos. 4, 5 and 6, said polynucleotide being chromosomally integrated or extrachromosomally present and the host cell being a plant cell, and that optionally the host cell additionally overexpresses an enzyme recycling a cofactor required for the oxygenase, in particular an enzyme converting NADP+ or NAD+ to NADPH or NADH, respectively.

An enzyme converting NADP+ or NAD+ to NADPH or NADH, respectively, and cofactors required therefor can be taken from the prior art, for instance from Torres Pazmino et al. 2008 (Angew. Chem. 47(12); 2275-8). Enzymes converting NADP+ or NAD+ to NADPH or NADH, respectively, are preferably selected so as to be usable without any problems in the food and/or feed industries and, in particular, comply with the respective food and/or feed regulations. Thus, it is, for instance, possible to use an NADPH-dependent xylose reductase, in particular from *Pichia stipitis*, which uses as substrate xylitol, which is admitted as feed additive, as said enzyme converting NADP+ to NADPH. Alternatively, an NAD(P)H-converting mannitol dehydrogenase from *Lactobacillus* sp. can be used, wherein mannitol, which is admitted as feed additive, can be used as substrate.

In a preferred manner, it is possible to prepare, or express, as fusion protein the polypeptide for detoxifying ZEN and an enzyme capable of recycling the cofactor. It is thereby possible to provide the two enzymatic activities in a joint process, in particular a biotechnological upstream and downstream process. When applying such a fusion protein, it is, moreover, ensured that the cofactor circulating between the two oxidation steps remains in spatial proximity to the polypeptide for detoxifying ZEN.

If the host cell is a plant cell, such a transgenic host cell enables the production of seed comprising said transgenic plant cell.

Finally, the present invention aims to provide an additive that enables the rapid and reliable detoxification, defined as reduction of the estrogenic activity, of ZEN in a defined or complex matrix, such as, for instance, animal feeds or food products.

To solve this object, a zearalenone-detoxifying additive is provided, which additive comprises at least one polypeptide being a monooxygenase converting the keto group in position 7 of zearalenone into an ester group, which monooxygenase preferably comprises an amino acid sequence selected from SEQ ID Nos. 1, 2 and 3 or a functional variant thereof, the functional variant and at least one of the amino acid sequences having a sequence identity of at least 60%, and optionally at least one adjuvant selected from the group consisting of vitamins, minerals, enzymes, further components for detoxifying mycotoxins and cofactors, in particular NADPH and/or NADH, enzyme preparations such as proteases, amylases, cellulases or glucanases, hydrolases, lipolytic enzymes, mannosidases, oxidases, oxidoreductases, phytases, xylanases and/or combinations thereof, mycotoxin-detoxifying enzymes such as aflatoxin oxidase, ergotamine hydrolases, ergotamine amidases, ochratoxin amidases, fumonisin carboxylesterases, fumonisin aminotransferases, aminopolyol aminoxidases, deoxynivalenol epoxide hydrolases; mycotoxin-detoxifying microorganisms; mycotoxin-binding components such as microbial cell walls, and inorganic materials such as bentonite. Such an additive in a food or feed product directly enables the one-step biochemical conversion of ZEN to a zearalenone derivative, namely iZOM, the toxicity of which is lower by a factor of about 100 than that of zearalenone. By using such an additive, it will be ensured that the major portion of the amounts of ZEN contained, for instance, in food or feed products will most certainly be oxidized to iZOM, thus preventing the occurrence of any harmful effect on the organism of a subject receiving such food or feed products.

The additive, in addition to a polypeptide according to the invention, may, for instance, also comprise as adjuvant an enzyme preparation in which at least one enzyme is further contained, which, for instance, participates in the degradation of proteins, e.g. proteases, or which participates in the metabolism of starch or fiber or fat or glycogen, e.g. amylases, cellulases or glucanases, as well as, for instance, hydrolases, lipolytic enzymes, mannosidases, oxidases, oxidoreductases, phytases, xylanases and/or combinations thereof.

Further possible adjuvants usable according to the invention include enzyme preparations that, in addition to at least one polypeptide according to the invention, contain at least one component for detoxifying mycotoxins different from zearalenone, such as a mycotoxin-detoxifying enzyme like aflatoxin oxidase, ergotamine hydrolases, ergotamine amidases, ochratoxin amidases, fumonisin carboxylesterases, fumonisin aminotransferases, aminopolyol aminoxidases, deoxynivalenol epoxide hydrolases; and/or at least one mycotoxin-detoxifying microorganism and/or at least one mycotoxin-binding component e.g. microbial cell walls, or inorganic materials such as bentonite.

Furthermore, the polypeptide is contained in the adjuvant in a concentration enabling the rapid conversion of ZEN to the non-toxic or significantly less toxic metabolite iZOM, in particular already prior to its resorption by the body of a subject, in particular mammal, eating contaminated feed or food.

The polypeptide may be present in the composition in encapsulated or coated form, wherein standard methods such as described, for instance, in WO 92/12645 can be used for encapsulating or coating. Such encapsulation or coating enables the polypeptide to be transported to its place of use without change, in particular degradation or damage, such that the polypeptide will not start acting before the dissolution of its protective coat, e.g. in the digestive tract of animals, thus achieving an even more selective, rapid and complete transformation of ZEN even in acid, protease-rich and anaerobic environments. By such encapsulation or coating, it is, moreover, also possible to enhance the temperature stability of the polypeptide in the additive.

The encapsulated or coated polypeptide can be further processed to premixes using adjuvants common in the feed industry.

The invention further relates to the use of an isolated polynucleotide encoding at least one polypeptide according to the invention and having a degree of sequence identity of at least 60% with at least one nucleotide sequence selected from the group consisting of SEQ ID Nos. 4, 5 and 6 for preparing a zearalenone-detoxifying monooxygenase, and to the use of an isolated polynucleotide encoding at least one polypeptide according to the invention and having a degree of sequence identity of at least 60% with at least one nucleotide sequence selected from the group consisting of SEQ ID Nos. 4, 5 and 6 in a method for preparing a zearalenone-detoxifying monooxygenase.

The present invention, moreover, relates to the use of the additive for detoxifying zearalenone in feed products, in particular for pigs, poultry and aquaculture; in food products; or in distillers dried grains with solubles. The use according to the invention of the additive enables the ZEN contained in the food or feed product or DDGS to be oxidized to iZOM, and hence detoxified, by converting the keto group in position 7 into an ester group, such detoxification being already feasible at low polypeptide concentrations in contaminated feed or food products.

The amount of polypeptide per ton of feed or food or DDGS lies within a range from about 1 g to about 500 g, the encapsulated or coated polypeptide ranging from about 20 g to about 3000 g, the premix ranging from about 200 g to about 10 kg, or the additive ranges from about 5 mg to about 10 kg. This enables the ZEN contained in feed or food products, which may be present in concentrations up to 10,000 µg/kg, to be converted to iZOM for the major portion.

If the additive is used in starch liquefaction processes, in saccharification processes, in biogas processes, or in fermentation processes such as the mashing or fermentation process in the production of bioethanol, it will be safeguarded that ZEN contained in the products used for the processes or resulting therefrom, such as DDGS or starch, will be converted to iZOM such that no health-damaging amounts of ZEN will remain intact.

The present invention further aims to provide a method for preparing a zearalenone-detoxifying monooxygenase that enables the rapid and reliable conversion of ZEN to a non-toxic derivative, namely iZOM.

To solve this object, the method is conducted such that an isolated polynucleotide comprising a nucleotide sequence encoding at least one polypeptide according to any one of claims 1 to 4 and/or having a degree of sequence identity of at least 60% with at least one nucleotide sequence selected from the group consisting of SEQ ID Nos. 4, 5 and 6 is chromosomally integrated into a transgenic host cell or extrachromosomally provided, that the host cell is a prokaryotic or eukaryotic cell, in particular a yeast or a plant cell, and that optionally an enzyme recycling a cofactor required for the oxygenase, in particular an enzyme converting NADP+ or NAD+ to NADPH or NADH, respectively, is additionally overexpressed in the host cell. Such an isolated polynucleotide encoding a zearalenone-detoxifying polypeptide can further be used for preparing a host cell in such a manner that the host cell expresses the isolated polynucleotide, which comprises a nucleotide sequence encoding at least one polypeptide according to the claims and/or having a degree of sequence identity of at least 60% with at least one nucleotide sequence selected from the group consisting of SEQ ID Nos. 4, 5 and 6, wherein the polynucleotide is chromosomally integrated or extrachromosomally provided and the host cell is a prokaryotic or eukaryotic cell, in particular a yeast or a plant cell, and optionally the host cell additionally overexpresses an enzyme recycling a cofactor required for the oxygenase, in particular an enzyme converting NADP+ or NAD+ to NADPH or NADH, respectively.

In that the zearalenone is converted to iZOM, and hence detoxified, by the addition of a polypeptide, in particular a monooxygenase, in a one-step enzymatic oxidation reaction, wherein the keto group in position 7 of the zearalenone is converted into an ester group, and that optionally a cofactor oxidized in the reaction, in particular NADP+ or NAD+, is reduced to NADPH or NADH, respectively, by a further enzyme, not only the rapid incorporation of the oxygen atom forming the ester group together with the keto group in position 7 will be guaranteed, but it will above all be ensured that the reaction will run to completion and zearalenone will be completely converted to iZOM, which is less toxic by a factor of about 100. NADP+ or NAD+ can be converted or recycled to NADPH or NADH, respectively, by the already described enzymatic systems.

In this case, a polypeptide having an amino acid sequence selected from SEQ ID Nos. 1, 2 and 3, or a functional variant thereof, can be used as polypeptide for the enzymatic detoxification of zearalenone, wherein the functional variant and at least one of the amino acid sequences have a sequence identity of at least 60%. When using a polypeptide having an amino acid sequence selected from SEQ ID Nos. 1, 2 and 3, a particularly complete detoxification of zearalenone has been observed.

The method according to the invention can be applied both in an additive per se and in a transgenic host cell, a transgenic plant, or in seeds, and regardless of the place of use will lead to consistently good results and, in particular, a complete transformation of zearalenone to iZOM.

In this case, the method can be conducted such that the polypeptide, or the additive, is mixed with a feed or food product contaminated with zearalenone, the obtained mixture is contacted with moisture, and the polypeptide, or the additive, detoxifies the zearalenone contained in the contaminated feed or food product. With moist feed or food products, such as mash or pulp, the conversion of zearalenone to iZOM takes place in the feed or food product prior to its oral intake so as to ensure that the harmful effects of zearalenone on humans and animals will be largely eliminated. By moisture, the presence of water or a water-containing liquid is understood, this also encompassing, for instance, saliva or other liquids present in the digestive tract.

The method according to the invention can also be conducted such that the feed or food product is pelletized prior to its oral intake.

According to a further development of the invention, the method for preparing a transgenic host cell is conducted such that an isolated polynucleotide comprising a nucleotide sequence encoding at least one polypeptide according to any one of claims 1 to 4 and/or having a degree of sequence identity of at least 60% with at least one nucleotide sequence selected from the group consisting of SEQ ID Nos. 4, 5 and 6 is chromosomally integrated into the host cell or extrachromosomally provided, that the polynucleotide is expressed in the host cell, that a prokaryotic or eukaryotic cell, in particular a yeast cell or a plant cell, is used as said host cell, and that optionally an enzyme recycling a cofactor required for the oxygenase, in particular an enzyme converting NADP+ or NAD+ to NADPH or NADH, respectively, is additionally overexpressed in the host cell.

Similarly, the invention relates to the use of a transgenic host cell for preparing a zearalenone-detoxifying monooxygenase, which is characterized in that an isolated polynucleotide comprising a nucleotide sequence encoding at least one polypeptide according to the claims and/or having a degree of sequence identity of at least 60% with at least one nucleotide sequence selected from the group consisting of SEQ ID Nos. 4, 5 and 6 is chromosomally integrated into the host cell or extrachromosomally provided, that the polynucleotide is expressed in the host cell, that a prokaryotic or eukaryotic cell, in particular a yeast cell or a plant cell, is used as said host cell, and that optionally an enzyme recycling a cofactor required for the oxygenase, in particular an enzyme converting NADP+ or NAD+ to NADPH or NADH, respectively, is additionally overexpressed in the host cell.

BRIEF DESCRIPTION OF THE DRAWINGS

In the following, the invention will be explained in more detail by way of exemplary embodiments and drawings. Therein.

FIG. 4 shows the estrogenic activity of ZEN (FIG. 4A) and of iZOM (FIG. 4B).

DETAILED DESCRIPTION OF THE INVENTION

Unless indicated in more detail, all molecular-biological and microbiological operations were performed using standard techniques (Methods in Enzymology, Volume 194, Pages 3-933 (1991); Guide to Yeast Genetics and Molecular Biology. Edited by Christine Guthrie, Gerald R. Fink. ISBN: 978-0-12-182095-4; J. Sambrook et al. 2012, Molecular Cloning, A Laboratory Manual 4th Edition, Cold Spring Harbor).

Example 1

Formation of iZOM from ZEN in a One-Step Reaction

The yeast strain YZGA515 (Saccharomyces cerevisiae modified by inactivation of the ABC transporter gene PDR5 (Poppenberger et al. 2003, J. Biol. Chem., 278 (48) 47905-14) for the enhanced absorption of zearalenone (ZEN)) was transformed by the plasmid pCS57 using standard techniques. pCS57 is a plasmid derived from the yeast expression plasmid pADH-FW (Mitterbauer et. al 2002, Appl. Environ. Microbiol.; 68 (3), 1336-1346) with LEU2 as selection marker and ADH1 promoter.

In the test setup, the yeast strain YZGA515 was transformed with the pCS57 vector additionally containing the polynucleotide of SEQ ID No. 4 as BamHI-XhoI fragment after the strongly constitutive ADH1 promoter (alcohol dehydrogenase 1). This enabled the formation of the polypeptide of SEQ ID No. 1.

The yeast strain YZGA515 with the empty vector (pADH-FW without the polynucleotide of SEQ ID No.4) was transformed as negative control.

The transgenic yeasts (test setup and negative control) were cultivated in SC-LEU medium (Sherman 1991, Methods Enzymol., 194, 3-21), centrifuged and resuspended in fresh SC-LEU medium at a concentration of 2 mg/l ZEN, wherein a cell density of OD600=4 was adjusted in both cases. After various incubation times, samples were taken, supplemented with 1 volume methanol, and the intracellular processes were thus stopped. The cell suspension was cleared by centrifugation, and the resulting supernatants were used for HPLC-MS measurements. The measurements, as described above, comprised the starting substance zearalenone (ZEN) and the transformation product ZOM-1 formed by Trichosporon mycotoxinivorans (Vekuri et al. 2010, Appl. Environ. Microbiol. 76(7) 2353-9).

Figure 1:
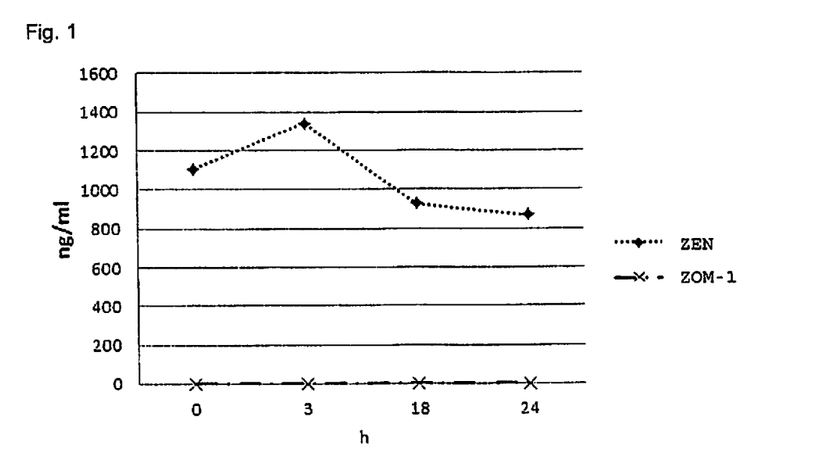
FIG. 1 depicts the partial transformation of ZEN in the negative control by S. cerevisiae.

In the negative control transformed with the empty vector, no ZOM-1 and, in particular, no iZOM was formed. The respective HPLC analysis data are illustrated in FIG. 1, the y-axis indicating nanogram per milliliter (ng/ml) and the x-axis indicating the time in hours (h).

Figure 2:
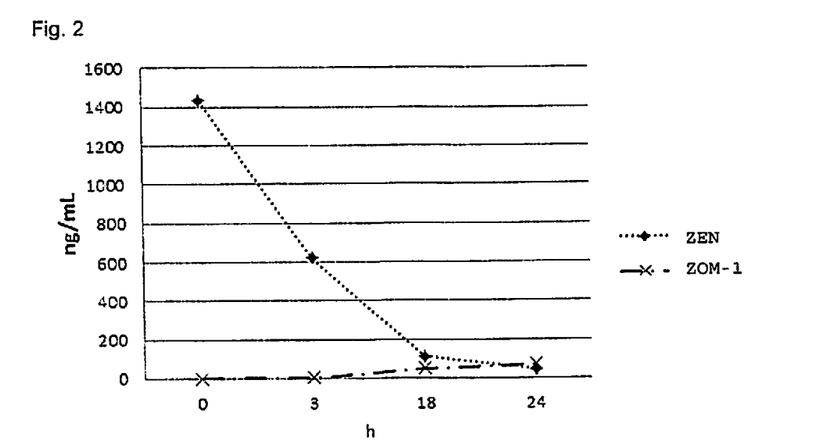
FIG. 2 depicts the transformation of ZEN in the test setup by S. cerevisiae, which expresses the polypeptide of SEQ ID No. 1.

By contrast, zearalenone was significantly more rapidly transformed in the test setup, and a new metabolite with the expected mass of the intermediate postulated by Vekiru et al. (2010) and referred to as iZOM below was identified. In addition, ZOM-1 was also detectable, which clearly suggested that a hydrolysis of iZOM to ZOM had occurred to some extent. The respective HPLC analysis data are illustrated in FIG. 2. Compared to the negative control, a much smaller amount of ZEN was measured, the y-axis indicating nanogram per milliliter (ng/ml) and the x-axis indicating the time in hours (h).

In a further test setup, the metabolite iZOM was additionally measured quantitatively. Table 1 shows the molar balance of the metabolization of ZEN. From this, it is clearly apparent that the major portion of the used zearalenone (ZEN) was already converted to iZOM after 6 hours. The small shortfall in the balance is explainable by the formation of further metabolites and the method-related analytical unsharpnesses. The results clearly show that the polypeptide of SEQ ID No. 1 is able to convert ZEN to its metabolite iZOM.

TABLE 1

Molar balance of the metabolization of ZEN in test setup

| Time [h] | ZEN [nM] | ZOM-1 [nM] | iZOM [nM] |
|---|---|---|---|
| 0 | 3364 | 0 | 0 |
| 6 | 172.1 | 0 | 2163.1 |
| 24 | 4.8 | 214.8 | 2068.2 |

Example 2

Identification of the Chemical Structure of iZOM

The chemical structure of the metabolite iZOM (FIG. 3) could be determined by NMR measurements of the isolated and purified metabolite. For measuring the NMR spectra, a sufficient amount of iZOM was prepared from several liters of the culture filtrate of a yeast culture (SC-LEU as described in Example 1). iZOM was purified by solid phase extraction and subsequent preparative HPLC.

The use of the isolated reference substance for iZOM on the one hand allowed for the tracing of the conversion of ZEN to iZOM (cf. Example 1) and, on the other hand, enabled the clarification of the chemical structure by NMR.

The NMR spectra for identifying iZOM were obtained in a CD3OD solution using a Bruker Avance DRX-400 FT NMR spectrometer at room temperature (20° C.) with a 5 mm inverse broadband z-gradient probe head. The chemical displacements were established based on the residual solvent resonance (3.31 ppm for $^1$H NMR, 49.15 ppm for $^{13}$C NMR). All pulse programs were taken from the Bruker software library. The NMR data were evaluated by means of TopSpin 1.3 (Bruker BioSpin GmbH). The determination of the complete structure and the assignment of signals were performed based on $^1$H, $^{13}$C-APT, $^1$H$^1$H correlation spectroscopy (COSY), $^1$H$^{13}$C heteronuclear single quantum correlation spectra (HSQC), and $^1$H$^{13}$C heteronuclear multiband correlation spectra (HMBC).

Figure 3:
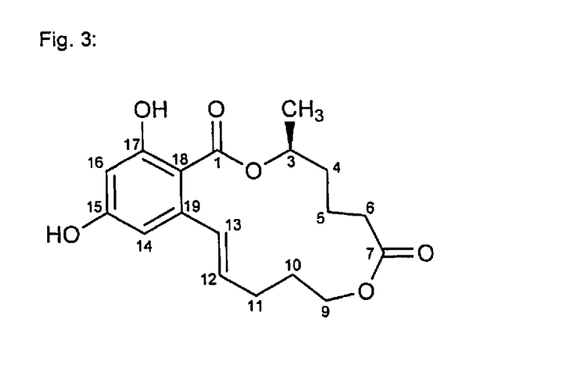
FIG. 3 illustrates the chemical structure of iZOM.

The NMR spectroscopy data of iZOM show two essential differences as compared to ZEN. These confirm the conversion of the keto group to an ester group. The differences substantially comprise the shift of the carbonyl carbon atom from 212 ppm in ZEN (typical of a ketone) to 175 ppm (typical of a carboxylic acid derivative) and the shift of the adjacent CH$_2$ group from 36 ppm and 2.90/2.30 ppm (position 8 in ZEN) to 65 ppm and 4.20/4.05 (position 9 in iZOM) for $^{13}$C and $^1$H, respectively, caused by the adjacent oxygen atom. Unlike the open ring of ZOM1, the macrocyclic ring in iZOM is still intact as evidenced by a long-range correlation between C7 and H9. The NMR data are indicated in Table 2. The chemical structure of iZOM is illustrated in FIG. 3.

TABLE 2

$^1$H and $^{13}$C NMR date for identifying iZOM

| Position | $^1$H δ (ppm) | Multiplicity, J (Hz) | $^{13}$C δ (ppm) |
|---|---|---|---|
| 1 | — | | 172.9 |
| 3 | 5.14 | m | 74.2 |
| 3-CH$_3$ | 1.36 | d, 6.2 | 20.2 |
| 4 | 1.65-1.80 | m | 36.5 |
| 5 | 1.90, 1.76 | m | 23.1 |
| 6 | 2.30-2.45 | m | 35.8 |
| 7 | — | | 175.4 |
| 9 | 4.18, 4.05 | m | 64.6 |
| 10 | 1.75-1.90 | m | 28.9 |
| 11 | 2.30-2.50 | m | 30.8 |
| 12 | 5.93 | ddd, 15.4, 8.3, 6.1 | 132.4 |
| 13 | 7.00 | d, 15.4 | 133.2 |
| 14 | 6.40 | d, 2.2 | 109.6 |
| 15 | — | | 165.0 |
| 16 | 6.19 | d, 2.2 | 103.3 |
| 17 | — | | 165.6 |
| 18 | — | | 104.9 |
| 19 | — | | 143.9 |

Example 3

Strongly Reduced Estrogenic Activity of iZOM as Compared to ZEN

The purified metabolite iZOM as described in Example 2 was used to determine its toxicity, expressed by its estrogenic activity, and compared to that of zearalenone.

For measuring the estrogenic activity, a specially prepared reporter yeast strain, YZHB817 (Bachmann, H.: Phenotypic detection of zearalenone in Saccharomyces cerevisiae. Master thesis BOKU Vienna, 2003) was used. This strain is derived from yeast-two hybrid strain PJ69-4a (MATa trp1-901 leu2-3,112 ura3-52 his3-200 gal4-(deleted) gal80(deleted) LYS2::GAL1-HIS3 GAL2-ADE2 met2::GAL7-lacZ) (James et al. 1996, Genetics; 144(4), 1425-1436). PJ69-4a was further developed by the disruption of the ABC transporters PDR5 and SNQ2. Strains with such double mutations pdr5 and snq2 exhibit a particularly high ZEN absorption (Mitterbauer et al. 2003, Appl. Environ. Microbiol.; 69(2), 805-811). This strain was subsequently transformed with an expression vector (pTK103) that triggers the production of a fusion protein containing the hormone-dependent activation domain of the human estrogen receptor alpha and the DNA binding domain of the yeast Gal4 protein, in order to obtain the strain YZHB817.

In the presence of estrogenic substances, the yeast strain YZHB817 induces the expression of the GAL7 lacZ reporter gene, whose product, the enzyme beta-galactosidase, is easy to measure by the hydrolyzation of the chromogenic substrate ONPG (ortho-nitrophenyl-beta-galactoside) at 420 nm (Current Protocols in Molecular Biology, Chapter 13, Yeast (Eds. Lundblad V, Struhl, K.)).

100 ml of the estrogenic test solution (ZEN or iZOM) were dissolved in 50% ethanol, mixed with 1.9 ml of the yeast culture of strain YZGA817 in SC-TRP medium at a cell density of OD$_{600}$=0.1, and incubated for 18 hours at 30° C. and 180 rpm. After this, the OD$_{600}$ of the culture was determined, and the cell pellet (10 min, 13 krpm) of 1 ml was resuspended in 500 ml Z buffer and permeabilized with 25 μl chloroform. The enzyme reaction was started by the addition of 100 μl ONPG solution (4 mg/ml) and stopped after yellow coloring upon addition of 250 μl of a 1M Na$_2$CO$_3$ solution. The supernatant was measured at 420 nm, and the relative units (based on the used cell amount) were calculated as:

$$RU=(OD_{420}\times 1000)/(OD_{600}\times \text{incubation time in min})$$

Figure 4A:
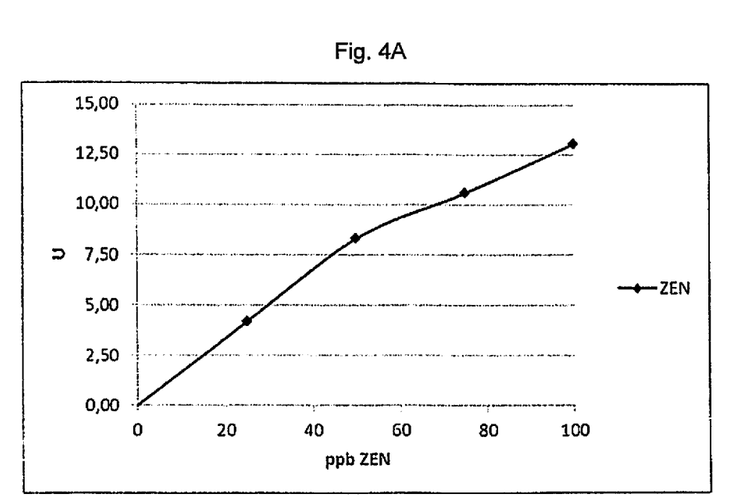
Figure 4B:
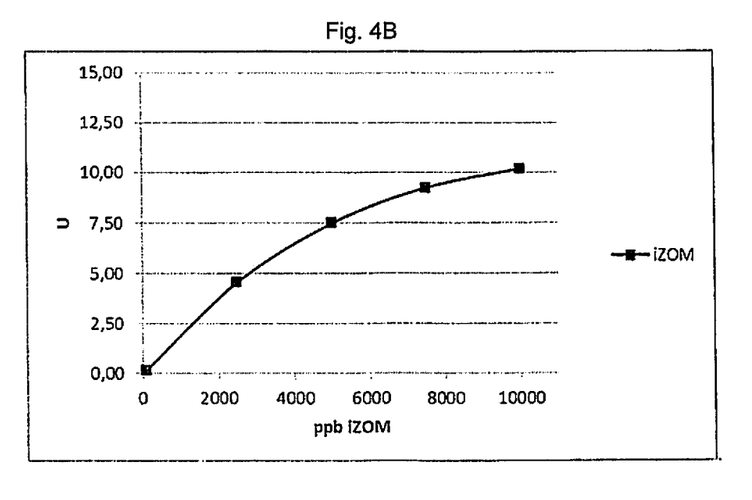

As illustrated in FIG. 4, ZEN induces the expression of the GAL7-lacZ reporter gene in the low ppb range, thus approximately 45 ppb ZEN are necessary to express 7.5 relative units of beta-galactosidase (FIG. 4A). By contrast, iZOM exhibits a far lower estrogenicity. In comparison, about 500 ppb were required to achieve approximately the same effect (FIG. 4B). Hence results that iZOM has an estrogenic activity approximately reduced by a factor 100 as compared to ZEN.

Example 4

Determination of the Sequence Identity

The determination of the percentual sequence identity of the polypeptides with the amino acid sequences SEQ ID Nos. 1, 2 and 3 relative to one another was performed by the alignment of two sequences using the program BLAST (Basic Local Alignment Search Tool), in particular BLASTP, which can be used on the homepage of the National Center for Biotechnology Information (NCBI; www.ncbi.nlm.nih.gov). It is thereby possible to compare two or several sequences with one another according to the algorithm of Altschul et al., 1397 (Nucleic Acids Res. (1997) 25: 3389-3402). The base adjustments were used as program adjustments, but in particular: "max target sequence"=100; "expected threshold"=10; "word size"=3; "matrix"= BLOSOM62; "gap costs"="Existence: 11; Extension: 1"; "computational adjustment"="Conditional compositional score matrix adjustment". The sequence identity between the sequences of SEQ ID No. 1 and SEQ ID No. 3 is 73%.

This application incorporates by reference the electronically submitted Sequence Listing filed on Jul. 9, 2020 in ASCII text file (CRF format) with the file name of P75529US0_SEQ_LIST_ST25.txt, created on May 1, 2017 and with the size of 11,026,432 bytes.

The invention claimed is:

1. A method for enzymatic detoxification of zearalenone by a recombinant isolated polypeptide comprising the step of reacting the polypeptide with zearalenone, wherein the polypeptide is a monooxygenase converting the keto group in position 7 of zearalenone into an ester group, and wherein the polypeptide comprises the amino acid sequence of SEQ ID NO: 1, SEQ ID NO: 2 or SEQ ID NO: 3 or an amino acid sequence having at least 90% sequence identity to the amino acid sequence of SEQ ID NO: 1, SEQ ID NO: 2 or SEQ ID NO: 3; wherein the monooxygenase is a Baeyer-Villiger monooxygenase and a cyclohexanone monooxygenase.

2. A method for enzymatic detoxification of zearalenone comprising the following steps:

preparing a recombinant isolated polypeptide by utilizing a yeast strain, which is transformed with a polynucleotide for expressing the polypeptide; and reacting the polypeptide with zearalenone, wherein the polypeptide is a monooxygenase converting the keto group in position 7 of zearalenone into an ester group, and wherein the polypeptide comprises the amino acid sequence of SEQ ID NO: 1, SEQ ID NO: 2 or SEQ ID NO: 3 or an amino acid sequence having at least 90% sequence identity to the amino acid sequence of SEQ ID NO: 1, SEQ ID NO: 2 or SEQ ID NO: 3; wherein the monooxygenase is a Baeyer-Villiger monooxygenase and a cyclohexanone monooxygenase.

* * * * *

SEQUENCE LISTING

```
<160> NUMBER OF SEQ ID NOS: 6

<210> SEQ ID NO 1
<211> LENGTH: 630
<212> TYPE: PRT
<213> ORGANISM: Trichosporon mycotoxinivorans

<400> SEQUENCE: 1

Met Thr Leu Glu Ala Ile Pro Val Pro Glu Glu Thr Pro Ala Gln Thr
1               5                   10                  15

Val Pro Thr Ala Pro Leu Ser Glu Glu Glu Arg Glu Ala Leu Lys His
            20                  25                  30

Arg Tyr Arg Ala Glu Arg Asp Lys Arg Ile Arg Glu Asp Gly Ile Lys
        35                  40                  45

Gln Tyr Arg Ser Leu Glu Gly Leu Leu Asp Val Asp Asp Thr Lys Asp
    50                  55                  60

Pro Tyr Thr Pro Val Lys Pro Arg Glu Pro Leu Asn Asp His Val Asp
65                  70                  75                  80

Phe Leu Phe Leu Gly Gly Gly Phe Ala Gly Leu Ile Val Cys Ser His
                85                  90                  95

Leu Lys Lys Thr Gly Phe Asn Asp Phe Arg Ile Ile Glu Ser Gly Gly
            100                 105                 110

Asp Phe Gly Gly Val Trp Tyr Trp Asn Arg Phe Pro Gly Ala Met Cys
        115                 120                 125

Asp Thr Ala Ala Met Val Tyr Leu Pro Leu Leu Glu Glu Thr Gly Thr
    130                 135                 140

Val Pro Ser Ala Lys Tyr Val Arg Gly Pro Glu Ile Leu Ala His Ala
145                 150                 155                 160

Gln Arg Ile Ala Arg Thr Phe Asp Leu Tyr Pro His Ala Leu Phe His
                165                 170                 175

Thr His Leu Glu Ser Leu Thr Trp Asp Glu Glu Gln Gly Val Trp Lys
            180                 185                 190

Val Lys Thr Arg Gln Gly Asp Ser Phe Thr Ala Thr His Val Gly Met
        195                 200                 205

Gly Thr Gly Pro Leu Asn Lys Pro His Leu Pro Gly Ile Pro Gly Ile
    210                 215                 220

Glu Lys Phe Lys Gly Lys Ala Met His Thr Ala Arg Trp Asp Phe Ala
225                 230                 235                 240
```

Thr Thr Gly Gly Gly Trp Asn Gly Glu Val Met Gly Leu Lys Asp
            245                 250                 255

Lys Arg Val Gly Val Ile Gly Thr Gly Ala Thr Gly Ile Gln Ala Ile
            260                 265                 270

Pro Glu Leu Gly Arg Asp Ser Gly Glu Leu Phe Val Phe Gln Arg Thr
            275                 280                 285

Pro Ser Ala Val Ala Val Arg Gly Asn His Pro Ile Asp Pro Glu Trp
        290                 295                 300

Phe Ala Ser Leu Asp Lys Gly Trp Gln Thr Lys Trp Asn Arg Asn Phe
305                 310                 315                 320

Ile Gln Leu Met Ser Ser Gly Met Ala Glu Asn Asp Tyr Val Arg Asp
                325                 330                 335

Gly Trp Thr Asp Gly Val Lys Arg Ile Thr Ala Arg Met Phe Ala Glu
                340                 345                 350

Ala Ala Lys Ala Gly Arg Asp Pro Ser Thr Leu Ser Phe Asp Asp Phe
            355                 360                 365

Leu Ala Ala Tyr His Leu Ser Asp Asp Glu Tyr Met Thr Ala Val Arg
        370                 375                 380

Asn Arg Thr Asn Glu Val Val Asn Asp Pro Lys Thr Ala Asp Gly Leu
385                 390                 395                 400

Lys Ala Trp Tyr Arg Gln Phe Cys Lys Arg Pro Cys Phe His Asp Glu
                405                 410                 415

Phe Leu Ala Thr Phe Asn Arg Pro Thr Val His Leu Val Asp Thr Asn
                420                 425                 430

Gly Gln Gly Val Thr Glu Val Asp Glu Thr Gly Val Trp Ala Asn Gly
            435                 440                 445

Gln His Tyr Asp Leu Asp Ile Ile Val Tyr Ala Thr Gly Phe Glu Phe
        450                 455                 460

Asn Ser Glu Trp Thr Tyr Lys Ser Gly Met Glu Val Tyr Gly Arg Asp
465                 470                 475                 480

Gly Leu Thr Leu Thr Gln Ala Trp Lys Asp Gly Met Lys Thr Tyr His
                485                 490                 495

Gly Met His Ile Asn Gly Phe Pro Asn Leu Phe Met Leu Gln Phe Gln
            500                 505                 510

Gln Gly Ser Ser Leu Ala Ser Asn Ile Thr Ser Asn Tyr Val Asp Ser
        515                 520                 525

Gly Tyr Thr Ile Ala Ala Ile Leu Asn Lys Lys Glu Leu Gly Ala
        530                 535                 540

Lys Thr Val Glu Val Pro Ala Asp Val Gln Ser Lys Trp Ile Glu His
545                 550                 555                 560

Leu Leu Thr Ala Asn Lys Gly Leu Ile Gly Gly Pro Glu Cys Thr Pro
                565                 570                 575

Gly Tyr Tyr Asn Asn Glu Gly Gln Glu Gly Leu Lys Glu Lys Leu
            580                 585                 590

Asn Gly Ala Arg Tyr Pro Ala Gly Ser Leu Ala Phe Phe Asp Tyr Ile
        595                 600                 605

Ala Glu Trp Arg Thr Asn Gly Lys Phe Glu Gly Leu Ala Phe Asp Gly
        610                 615                 620

Lys Gln Ile Ala Val Gln
625                 630

<210> SEQ ID NO 2
<211> LENGTH: 709

<212> TYPE: PRT
<213> ORGANISM: Trichosporon mycotoxinivorans

<400> SEQUENCE: 2

```
Met Ser Ala Ser Arg Pro Arg Gly Ser Pro His Tyr Leu Gly Asp Arg
1               5                   10                  15

Ser Thr Lys Ser Gly Leu Arg Arg Pro Phe Lys Arg Ser Lys Lys Asn
            20                  25                  30

Arg Ala Thr Asn Ala Val Phe Ser Gln Arg His Arg Lys Pro Thr Glu
        35                  40                  45

Gly Ala Gly Val Arg Gly Lys His Ser Cys Ser Val Ile Pro Asp Lys
    50                  55                  60

His Thr Ala Pro Trp Gly Pro Ala Ala Ala Glu Pro Gly Trp His Met
65                  70                  75                  80

Thr Leu Glu Ala Ile Pro Val Pro Glu Glu Thr Pro Ala Gln Thr Val
                85                  90                  95

Pro Thr Ala Pro Leu Ser Glu Glu Glu Arg Glu Ala Leu Lys His Arg
            100                 105                 110

Tyr Arg Ala Glu Arg Asp Lys Arg Ile Arg Glu Asp Gly Ile Lys Gln
        115                 120                 125

Tyr Arg Ser Leu Glu Gly Leu Leu Asp Val Asp Asp Thr Lys Asp Pro
    130                 135                 140

Tyr Thr Pro Val Lys Pro Arg Glu Pro Leu Asn Asp His Val Asp Phe
145                 150                 155                 160

Leu Phe Leu Gly Gly Gly Phe Ala Gly Leu Ile Val Cys Ser His Leu
                165                 170                 175

Lys Lys Thr Gly Phe Asn Asp Phe Arg Ile Ile Glu Ser Gly Gly Asp
            180                 185                 190

Phe Gly Gly Val Trp Tyr Trp Asn Arg Phe Pro Gly Ala Met Cys Asp
        195                 200                 205

Thr Ala Ala Met Val Tyr Leu Pro Leu Leu Glu Glu Thr Gly Thr Val
    210                 215                 220

Pro Ser Ala Lys Tyr Val Arg Gly Pro Glu Ile Leu Ala His Ala Gln
225                 230                 235                 240

Arg Ile Ala Arg Thr Phe Asp Leu Tyr Pro His Ala Leu Phe His Thr
                245                 250                 255

His Leu Glu Ser Leu Thr Trp Asp Glu Glu Gln Gly Val Trp Lys Val
            260                 265                 270

Lys Thr Arg Gln Gly Asp Ser Phe Thr Ala Thr His Val Gly Met Gly
        275                 280                 285

Thr Gly Pro Leu Asn Lys Pro His Leu Pro Gly Ile Pro Gly Ile Glu
    290                 295                 300

Lys Phe Lys Gly Lys Ala Met His Thr Ala Arg Trp Asp Phe Ala Thr
305                 310                 315                 320

Thr Gly Gly Gly Trp Asn Gly Glu Val Met Glu Gly Leu Lys Asp Lys
                325                 330                 335

Arg Val Gly Val Ile Gly Thr Gly Ala Thr Gly Ile Gln Ala Ile Pro
            340                 345                 350

Glu Leu Gly Arg Asp Ser Gly Glu Leu Phe Val Phe Gln Arg Thr Pro
        355                 360                 365

Ser Ala Val Ala Val Arg Gly Asn His Pro Ile Asp Pro Glu Trp Phe
    370                 375                 380

Ala Ser Leu Asp Lys Gly Trp Gln Thr Lys Trp Asn Arg Asn Phe Ile
385                 390                 395                 400
```

Gln Leu Met Ser Ser Gly Met Ala Glu Asn Asp Tyr Val Arg Asp Gly
            405                 410                 415

Trp Thr Asp Gly Val Lys Arg Ile Thr Ala Arg Met Phe Ala Glu Ala
            420                 425                 430

Ala Lys Ala Gly Arg Asp Pro Ser Thr Leu Ser Phe Asp Phe Leu
            435                 440                 445

Ala Ala Tyr His Leu Ser Asp Asp Glu Tyr Met Thr Ala Val Arg Asn
            450                 455                 460

Arg Thr Asn Glu Val Val Asn Asp Pro Lys Thr Ala Asp Gly Leu Lys
465                 470                 475                 480

Ala Trp Tyr Arg Gln Phe Cys Lys Arg Pro Cys Phe His Asp Glu Phe
            485                 490                 495

Leu Ala Thr Phe Asn Arg Pro Thr Val His Leu Val Asp Thr Asn Gly
            500                 505                 510

Gln Gly Val Thr Glu Val Asp Glu Thr Gly Val Trp Ala Asn Gly Gln
            515                 520                 525

His Tyr Asp Leu Asp Ile Ile Val Tyr Ala Thr Gly Phe Glu Phe Asn
            530                 535                 540

Ser Glu Trp Thr Tyr Lys Ser Gly Met Glu Val Tyr Gly Arg Asp Gly
545                 550                 555                 560

Leu Thr Leu Thr Gln Ala Trp Lys Asp Gly Met Lys Thr Tyr His Gly
            565                 570                 575

Met His Ile Asn Gly Phe Pro Asn Leu Phe Met Leu Gln Phe Gln Gln
            580                 585                 590

Gly Ser Ser Leu Ala Ser Asn Ile Thr Ser Asn Tyr Val Asp Ser Gly
            595                 600                 605

Tyr Thr Ile Ala Ala Ile Leu Asn Lys Lys Lys Glu Leu Gly Ala Lys
            610                 615                 620

Thr Val Glu Val Pro Ala Asp Val Gln Ser Lys Trp Ile Glu His Leu
625                 630                 635                 640

Leu Thr Ala Asn Lys Gly Leu Ile Gly Gly Pro Glu Cys Thr Pro Gly
            645                 650                 655

Tyr Tyr Asn Asn Glu Gly Gln Glu Gly Leu Lys Glu Lys Leu Asn
            660                 665                 670

Gly Ala Arg Tyr Pro Ala Gly Ser Leu Ala Phe Phe Asp Tyr Ile Ala
            675                 680                 685

Glu Trp Arg Thr Asn Gly Lys Phe Glu Gly Leu Ala Phe Asp Gly Lys
            690                 695                 700

Gln Ile Ala Val Gln
705

<210> SEQ ID NO 3
<211> LENGTH: 630
<212> TYPE: PRT
<213> ORGANISM: Trichosporon asahii

<400> SEQUENCE: 3

Met Thr Ile Asp His Ile Pro Glu Pro Thr Asp Tyr Lys Gln Thr Gln
1               5                   10                  15

Pro Val Ala Pro Leu Ala Asp Glu Glu Arg Gln Ala Leu Gln Ala Lys
            20                  25                  30

Tyr Arg Glu Glu Arg Asp Lys Arg Leu Arg Ala Asp Gly Ile Asn Gln
            35                  40                  45

Tyr Lys Pro Leu Gly Gly Ile Leu Lys Leu Asp Glu Asp Lys Asp Pro

-continued

```
                50                      55                      60
Tyr Thr Asp Val Gln Pro Arg Glu Pro Val His Asp His Val Asp Phe
 65                      70                      75                      80

Leu Phe Leu Gly Gly Gly Phe Ala Gly Leu Thr Val Cys Ala Lys Leu
                         85                      90                      95

Lys Gln Ala Gly Phe Asp Ser Ile Arg Ile Leu Glu Ser Gly Gly Asp
                        100                     105                     110

Phe Gly Gly Val Trp Tyr Trp Asn Arg Phe Pro Gly Ala Met Cys Asp
                        115                     120                     125

Thr Ala Ala Met Val Tyr Leu Pro Met Met Glu Glu Val Gly Thr Val
                        130                     135                     140

Pro Ser Ala Lys Tyr Val Arg Gly Pro Glu Ile Leu Ala His Ala His
145                     150                     155                     160

Arg Ile Ala Arg His Phe Asp Leu Tyr Pro His Ala Leu Phe Ser Thr
                        165                     170                     175

His Leu Glu Glu Leu Arg Trp Asp Glu Asp Arg Ser Val Tyr Val Val
                        180                     185                     190

Lys Thr Arg Glu Gly Asp Glu Phe Thr Ala Thr Asn Val Ala Met Gly
                        195                     200                     205

Thr Gly Pro Leu Asn Arg Pro His Leu Pro Gly Ile Pro Gly Leu Glu
                        210                     215                     220

Thr Phe Lys Gly Gln Ala Met His Thr Ala Arg Trp Asp Phe Gly Val
225                     230                     235                     240

Thr Gly Gly Gly Trp Asp Asp Glu Val Leu Glu Gly Leu Lys Asp Lys
                        245                     250                     255

Arg Val Gly Val Ile Gly Thr Gly Ala Thr Gly Val Gln Cys Ile Pro
                        260                     265                     270

Thr Leu Gly Arg Asp Ser Gly Ser Leu His Val Phe Gln Arg Thr Pro
                        275                     280                     285

Ser Ala Val Ala Ile Arg Gly Asn His Ala Ile Asp Lys Glu Trp Phe
                        290                     295                     300

Ser Gln Leu Asp Lys Gly Trp Gln Thr Lys Trp Leu Arg Asn Phe Cys
305                     310                     315                     320

Gln Leu Met Ser Thr Gly Tyr Ala Pro Val Asp Tyr Val His Asp Gly
                        325                     330                     335

Trp Thr Asp Gly Val Gln Arg Ile Thr Lys Arg Met Leu Glu Met Cys
                        340                     345                     350

Ala Lys Glu Gly Arg Ala Pro Thr Gly Met Ala Asp Tyr Met Lys Ala
                        355                     360                     365

Tyr His Leu Ser Asp Asp Glu Tyr Thr Thr Ala Val Arg Ala Arg Thr
                        370                     375                     380

Asp Glu Val Val Lys Asp Pro Glu Thr Ala Lys Leu Lys Ala Trp
385                     390                     395                     400

Tyr Arg Gln Phe Cys Lys Arg Pro Thr Phe His Asp Glu Tyr Leu Gln
                        405                     410                     415

Thr Phe Asn Arg Pro Asn Val Thr Leu Val Asp Thr Asp Gly Lys Gly
                        420                     425                     430

Val Glu Arg Ile Asp Glu Thr Gly Val Trp Ala Asn Gly Lys His Tyr
                        435                     440                     445

Asp Leu Asp Val Leu Val Tyr Ala Thr Gly Phe Glu Phe Asn Ser Glu
                        450                     455                     460

Tyr Thr Tyr Lys Ser Gly Leu Glu Val Tyr Gly Arg Gly Gly Arg Thr
465                     470                     475                     480
```

```
Leu Thr Asp Ala Trp Lys Asp Gly Met Gln Ser Phe Gln Gly Met His
            485                 490                 495

Val His Gly Phe Pro Asn Leu Phe Val Ile Gly Phe Ala Gln Gly Ser
        500                 505                 510

Ser Leu Ala Ser Asn Ile Thr Ser Asn Tyr Thr Glu His Gly Pro Thr
        515                 520                 525

Val Leu Ser Ile Leu Gln Lys Lys Lys Glu Leu Gly Ala Lys Thr Val
        530                 535                 540

Glu Val Pro Gln Lys Thr Gln Asp Asp Trp Ile Glu Leu Ile Leu Gln
545                 550                 555                 560

Gly Asp Arg Gly Ile Ile Gly Gly Pro Glu Cys Thr Pro Gly Tyr Tyr
                565                 570                 575

Asn Asn Glu Gly Gln Glu Gly Arg Arg Glu Arg Leu Asn Val Ala
            580                 585                 590

Arg Tyr Pro Ala Gly Pro Leu Ala Phe Phe Asp Tyr Ile Ala Glu Trp
        595                 600                 605

Arg Ala Asn Gly Lys Phe Glu Gly Leu Glu Phe Asp Gly Lys Pro Val
    610                 615                 620

Glu Ile Ala Ala Thr Leu
625                 630

<210> SEQ ID NO 4
<211> LENGTH: 1890
<212> TYPE: DNA
<213> ORGANISM: Artificial Sequence
<220> FEATURE:
<223> OTHER INFORMATION: Codon Optimiertes Polynukleotid des Polypeptids
      mit SEQ ID Nr. 1 zur Expression in Saccharomyces cerevisiae

<400> SEQUENCE: 4
atgactttgg aagctattcc agttccagaa gaaactccag ctcaaactgt tccaactgct      60
ccattgtctg aagaagaaag agaagccttg aaacatagat acagagccga agagataag     120 agaatcagag aagatggtat caagcaatac agatccttgg aaggtttgtt ggatgttgat    180
gataccaaag atccatacac tccagttaag ccaagagaac cattgaacga tcatgtcgat    240 ttttttgtttt tgggtggtgg ttttgctggt ttgatcgttt gttctcattt gaaaaagacc    300
ggtttcaacg acttcagaat cattgaatct ggtggtgatt cggtggtgt ttggtattgg     360 aatagatttc caggtgctat gtgtgatact gctgctatgg tttatttgcc tttgttggaa    420
gaaactggta cagttccatc tgctaaatat gttagaggtc cagaaatttt ggctcacgct    480
caaagaattg ctagaacttt tgacttgtac ccacatgctt gttccatac ccatttggaa      540 tctttgactt gggatgaaga acaaggtgtt tggaaagtta agaccagaca aggtgattct    600
ttcactgcta ctcatgttgg tatgggtact ggtccattga acaaaccaca tttgcctggt    660
attccaggta tcgaaaagtt taaggtaag gctatgcata ccgctagatg ggatttttgct    720 actactggtg gtggttggaa tggtgaagtt atggaaggtt taaaggataa agagttggt     780 gttattggta ctggtgctac tggtattcaa gctataccag aattgggtag agactccggt    840
gaatttattg ttttccaaag aacaccatcc gctgttgcag ttagaggtaa tcatccaatt    900
gatccagaat ggtttgcctc tttggataag ggttggcaaa caagtggaa cagaaacttt     960 attcaattga tgtcctccgg tatggccgaa aatgattacg ttagagatgg ttggactgat   1020
ggtgttaaga gaattactgc tagaatgttt gctgaagctg ctaaagctgg tagagatcca   1080
tctactttgt ctttcgatga tttcttggct gcctaccatt gtccgatga tgaatatatg    1140
```

```
actgccgtca gaaacagaac taacgaagtt gttaacgatc caaagactgc tgatggtttg    1200
aaagcttggt atagacaatt ctgcaaaaga ccatgcttcc acgatgaatt tttggctact    1260
tttaacagac caaccgttca cttggttgat acaaatggtc aaggtgttac tgaagttgac    1320
gaaaccggtg tttgggctaa tggtcaacat tacgatttgg atattatcgt ttacgccact    1380
ggtttcgaat tcaactctga atggacttac aagtctggta tggaagttta tggtagagat    1440
ggtttgacat tgactcaagc ttggaaagac ggtatgaaaa cctatcatgg tatgcacatt    1500
aacggtttcc caaacttgtt catgttgcaa ttccaacaag gttcctcttt ggcttctaac    1560
atcacttcta actacgttga ttccggttac accattgctg ctattttgaa caaaaagaaa    1620
gaattaggtg ccaagaccgt tgaagttcca gctgatgttc aatctaaatg gatcgaacat    1680
ttgttgaccg ctaacaaggg tttgattggt ggtccagaat gtactccagg ttactataac    1740
aatgaaggtc aagaagaagg tttgaaagaa aagttgaacg gtgctagata ccagctggt    1800 tcattggctt ttttcgatta cattgctgaa tggagaacta atggtaaatt cgaaggtttg    1860
gccttcgatg gtaaacaaat tgctgttcaa                                     1890

<210> SEQ ID NO 5
<211> LENGTH: 2127
<212> TYPE: DNA
<213> ORGANISM: Trichosporon mycotoxinivorans

<400> SEQUENCE: 5
atgtctgcta gtagaccgcg cggctcccca cattatctcg gtgaccggtc taccaaaagc      60
ggtctacgca gaccgtttaa acggtcgaaa agaacagag ccacgaacgc cgtgttttcc     120
cagcgccatc gcaagccaac cgaaggtgcc ggtgttcggg gtaaacacag ttgctcggtg    180
atccccgata agcacaccgc cccatggggc ccggccgccg ccgaacctgg atggcacatg    240
acactcgaag ctattcctgt tcccgaggag acgcccgcgc agaccgtccc caccgctccg    300
ctctcggagg aagagcgcga ggccttgaag caccgatacc gcgccgagag ggacaagcgt    360
atccgcgaag acggcatcaa gcagtaccgc tccctggagg gtcttctgga cgtcgacgac    420
accaaggacc cgtacacgcc cgtgaagcct cgtgagcccc tgaacgacca tgtcgacttc    480
ctgttcctgg gtggtgggtt cgccggcctc attgtctgct cccatctcaa aaagaccggc    540
ttcaacgatt tccgcatcat cgagtcgggc ggagactttg gaggtgtatg gtactggaac    600
cgcttccccg gcgccatgtg tgacaccgcc gcgatggtct acttgcccct cctcgaggag    660
acgggcaccg tgccgtcggc caagtatgtc cgtggcccag agattcttgc gcacgcgcag    720
cgcatcgctc gcacgtttga cctgtacccg cacgctctgt tccacacgca cctcgagtct    780
cttacgtggg acgaggagca gggcgtctgg aaggtcaaga cgcgccaggg cgactcgttc    840
acggcgaccc acgtgggcat gggcaccgga cctctcaaca agccccacct tcctggtatc    900
cccggtatcg aaaagttcaa gggcaaggcg atgcacactg cccgctggga cttgcgacg    960 acgggcggcg gctggaatgg agaagttatg gagggactca aggacaagcg cgtcggcgtg   1020
atcggtaccg gcgctaccgg catccaggcg attcccgagc tcggccgcga cagcggcgag   1080 ctttcgtgt tccagcgcac gccctccgct gtcgccgtcc gaggcaacca ccccatcgac   1140
cccgagtggt ttgcgagcct cgacaagggg tggcagacaa agtggaaccg taactttatc   1200
cagctcatga gctcgggcat ggccgagaac gactatgtcc gtgacggctg gaccgacggc   1260
gtcaagcgca ttacggccag gatgtttgcc gaggcggcaa aggctggtcg ggacccttcg   1320
```

-continued

```
actctgtcgt ttgatgactt ccttgcggcg taccatctct cggacgacga gtacatgaca       1380
gcggtacgca accgcactaa cgaagtcgtc aacgacccca agaccgccga cggtctcaag       1440
gcgtggtacc gccagttttg caagcgtccg tgcttccacg acgagttttt ggccaccttc       1500
aaccgcccta ccgtccacct cgtggacacc aacggccagg gcgtaaccga ggtcgacgag       1560
acgggcgtct gggccaacgg acagcactac gacctcgaca ttatcgtcta tgccactgga       1620
ttcgagttca actcggagtg gacatacaag tccggcatgg aggtgtacgg ccgcgacggg       1680 ctcacccctca cgcaggcgtg gaaggacggc atgaagacgt accacggcat gcacatcaac       1740
gggttcccca acctgttcat gcttcagttc cagcagggat cgtcgctcgc atccaacatt       1800
acatccaact atgtcgactc gggctacacc attgcggcga ttctcaacaa gaaaaaggag       1860
ctcggagcca agacggtcga ggtccccgcc gacgtccagt caaagtggat cgagcacctc       1920
ctcaccgcga acaagggcct gatcggagga ccagagtgca ccccggata ctacaacaac        1980 gagggccagg aggaaggcct caaggagaag ctcaacggag cacggtaccc tgcgggatct       2040
ctcgcattct ttgactacat cgccgagtgg cgtacaaacg gcaagtttga gggtcttgcg       2100
tttgatggaa agcagatcgc agtgcag                                          2127
```

<210> SEQ ID NO 6
<211> LENGTH: 1893
<212> TYPE: DNA
<213> ORGANISM: Trichosporon asahii

<400> SEQUENCE: 6

```
atgacgatcg accacatccc agagccgacg gactacaagc agacgcagcc cgtcgcgcct        60
ctggcggacg aggagcgcca ggcgctgcag gccaaatacc gcgaggagcg cgacaagcga       120
ctccgcgccc atggtattaa ccagtacaag cccctcggcg catcttgaa gctggacgag        180 gacaaggacc cgtacacgga cgtccagccg cgcgagccgg tccacgacca tgtcgacttt       240
ctgttccttg gcgtggcttt cgcgggcctg acggtgtgcg cgaagctgaa gcaggcgggc       300
tttgactcga tccgcatcct cgagagcgga ggcgactttg gcggcgtctg gtactggaac       360
cgcttccccg gcgccatgtg cgacacggcc gccatggtct acctccccat gatggaggag       420
gttggcacgg tgccctcggc caaatatgtc cgcggacccg agattctcgc ccacgcccac       480
cgcatcgcgc gccacttcga cctctacccc cacgctctgt tcagcaccca cctcgaggag       540
ctgcgctggg acgaggaccg cagcgtctac gttgtcaaga cgcgcgaggg cgacgagttc       600
acggcgacca acgtcgcgat gggcactgga ccccctgaacc gtccccacct gcccggtatc       660
cctggactgg agacattcaa gggccaggcg atgcacaccg ctcgctggga ctttggcgtg       720 accgcggag gctgggacga tgaggtcctc gagggttga aggacaagcg tgtcggtgtc        780
atcggcacgg gcgccacggg tgtgcagtgt atcccgactc ttggacgcga ctctggctcc       840
ctgcatgtgt tccagcgcac gccctctgcc gtcgctatcc gcggcaacca tgcgattgac       900
aaggagtggt tcagccagct ggacaagggg tggcagacca agtggctgcg caacttctgc       960
cagctcatgt cgaccgggta cgcccccgtc gattacgtcc acgacgggtg gaccgacggc      1020
gtgcagcgca tcacgaagcg catgctcgag atgtgcgcca aggaggggcg cgcgccgacc      1080
ggaatggcag actacatgaa ggcgtaccac ctcagcgacg acgagtacac caccgccgtg      1140
cgcgcccgca ccgacgaggt cgtcaaggat cccgaaacgg ccgacaagct gaaggcgtgg      1200
tacaggcagt tttgcaaacg ccccacccttt catgacgagt acttgcagac gttcaaccgg      1260
ccgaacgtta cgctcgtcga cacggacggc aagggcgtgg agcgcatcga cgagacgggc       1320
```

```
gtctgggcga acggcaagca ctacgacctc gacgtacttg tgtacgcgac aggcttcgag   1380
ttcaactcgg agtacacata caagtctggt ctcgaggtgt acggtcgcgg tgggcgcacg   1440
ctcaccgatg catggaagga cggcatgcag tccttccagg gcatgcacgt gcacgggttc   1500
ccgaacctgt tcgtgatcgg ttttgcgcag gggtcctcac tcgcgtccaa cattacgagc   1560
aactacaccg agcacgggcc cacggtcctc agcatcctgc agaagaagaa ggagctcggc   1620
gctaagacgg tcgaggtgcc ccagaaaacg caggacgact ggatcgaact catcctccag   1680
ggcgaccggg gcattattgg cggtcccgag tgcacacccg gctactacaa caacgagggc   1740
caggaggagg gccgtcgcga gcgcctcaat gttgcgcgat accccgctgg tccgctcgct   1800
ttcttcgact acatcgccga gtggcgcgcg aacggcaagt tcgagggcct cgagtttgat   1860
ggcaagccgg tcgagattgc cgcgactctg tag                                 1893
```